(12) United States Patent
Muehlradt

(10) Patent No.: US 6,573,242 B1
(45) Date of Patent: Jun. 3, 2003

(54) DIHYDROXYPROPYL CYSTEINE PEPTIDE AND AGENT CONTAINING THIS PEPTIDE

(75) Inventor: Peter F. Muehlradt, Braunschweig (DE)

(73) Assignee: Gesellschaft fuer Biotechnologische, Braunschweig (DE)

( * ) Notice: Subject to any disclaimer, the term of this patent is extended or adjusted under 35 U.S.C. 154(b) by 0 days.

(21) Appl. No.: 09/331,087

(22) PCT Filed: Dec. 17, 1997

(86) PCT No.: PCT/EP97/07090

§ 371 (c)(1),
(2), (4) Date: Aug. 18, 1999

(87) PCT Pub. No.: WO98/27110

PCT Pub. Date: Jun. 25, 1998

(30) Foreign Application Priority Data

Dec. 17, 1996 (DE) .......................................... 196 52 586

(51) Int. Cl.$^7$ ............................................. A61K 38/00
(52) U.S. Cl. ......................... 514/14; 514/16; 514/669; 514/667; 514/167; 514/772.3; 424/177; 424/486; 424/180.1; 424/182.1
(58) Field of Search ............................. 424/177, 180.1, 424/182.1, 486; 514/16, 14, 669, 667, 167, 772.3, 994; 435/6; 530/345, 350; 540/114, 94; 552/541, 548

(56) References Cited

U.S. PATENT DOCUMENTS

| | | | | |
|---|---|---|---|---|
| 4,439,425 A | * | 3/1984 | Tarcsay et al. .............. | 424/177 |
| 5,478,809 A | * | 12/1995 | Tanida et al. ................. | 514/16 |
| 5,583,198 A | * | 12/1996 | Whittaker .................... | 530/345 |
| 5,817,461 A | * | 10/1998 | Austin et al. .................. | 435/6 |
| 5,856,444 A | * | 1/1999 | Kawakita et al. ........... | 530/350 |
| 5,869,606 A | * | 2/1999 | Whittaker .................... | 530/345 |

FOREIGN PATENT DOCUMENTS

WO    96/16987    *    6/1996

OTHER PUBLICATIONS

Hoffman, W.D et al, Anesth Analg, 1993, vol. 77, pp. 613–624, Endotoxin in septic shock.*
Ellis, R.W.Ph.D., Chapter 29, pp. 568–574, New Technologies for making vaccines, Vaccines, WB Saunders Company, 1988.*
Boslego, JW et al, Chapter 17, pp. 211–223, Vaccines and Immunotherapy, 1991, Pergamon Press.*
Metzger et al, Journal of Peptide Science, May–Jun., vol. 1(3), pp. 184–190, 1995.*
Hall, R.E. et al, Biochemical Jorunal, vol. 319(3), pp. 919–927, (abstract) 1996.*

* cited by examiner

*Primary Examiner*—Lynette R. F. Smith
*Assistant Examiner*—Ginny Allen Portner
(74) *Attorney, Agent, or Firm*—Frommer Lawrence & Haug, LLP; Ronald R. Santucci

(57) ABSTRACT

The invention relates to a S-(2,3-dihydroxypropyl)-cysteine peptide which has two long-chain fatty acids bonded in the form of esters at the dihydroxypropyl group, and which has the following sequence:

```
Dhc GN NDE SNI SFK EK (SEQ ID No 1)
 1   5    10
```

The invention relates also to a composition comprising the mentioned peptide.

13 Claims, No Drawings

DIHYDROXYPROPYL CYSTEINE PEPTIDE AND AGENT CONTAINING THIS PEPTIDE

The macrophage-stimulating activity of mycoplasma has been known for a relatively long time; see Loewenstein et al. in Cellular Immunology, 77 (1983) 290–297. It has also been assumed and formally proved that lipoproteins from mycoplasma exhibit such an activity; see Herbelin et al. in Infect. lmmun., 62 (1994) 4690–4694 and Mühlradt et al. in Biochemistry, 35 (1996) 7781–7786. Lipoproteins from Gram-negative bacteria and analogues of those lipoproteins are likewise immunomodulators and have been described specifically as macrophage activators; see Melchers et al. in J. Exp. Med., 142 (1975) 473–482 and Hoffmann et al. in Immunobiol., 177 (1988) 158–170. Those species of lipoproteins carry an N-terminal S-(2,3-dihydroxypropyl)-cysteine group (Dhc) having three long-chain fatty acids, of which two are bonded in the form of esters and one is bonded in the form of an amide.

Lipoproteins and synthetic lipopeptide analogues have a half-maximum effective concentration (Max/2) of approximately $10^{-7}$ M; see Melchers et al. in J. Exp. Med., 142 (1975) 473–482 and Hoffmann et al in Biol. Chem. Hoppe Seyler, 370 (1989) 575–582.

Synthetic analogues without the amide fatty acid have a half-maximum effective concentration (Max/2) of approximately $10^{-8}$M; see Metzger et al. in J. Peptide Scie., 3 (1995) 184–190. Furthermore, in Tertahedron, 45 (1989) 6331–6360, 6352, Baschang described a taurine-modified lipoprotein (sodium sulphonate; CGP-31362) which, according to Dong et al. in J. Exp. Med., 177 (1993) 1071–1077. still has macrophage-activating action as from 1 to 10 ng/ml of from 1 to $10 \times 10^{-9}$ M. Finally, in J. Peptide Scie., 3 (1995) 184–190, Metzge describes a Dhc peptide having the amino acid sequence CFE PPP ATT T (SEQ ID NO: 2), two palmitoyl groups being bonded to the 2,3-dihydroxypropyl group. The half-maximum effective concentration (Max/2) of that known peptide is 16 ng/ml or $10 \times 10^{-9}$ M.

There is, however, still a need for effective lipopeptides.

According to the invention there is now proposed a S-(2,3-dihydroxypropyl)-cysteine peptide having two fatty acids, which may be identical or different, bonded to the dihydroxypropyl group in the form of esters, the peptide having the following amino acid sequences (SEQ ID NO 1):

```
DhcGN NDE SNI SFK EK
    1   5   10

Dhcys Gly Asn Asn Asp Glu Ser Asn Ile Ser Phe Lys Glu Lys
    1               5                  10
``` or an amino acid sequence that is identical to the sequence (SEQ ID NO 1) except that the two N-terminal amino acids in positions 2 and, optionally, 3 are missing and/or one or two C-terminal amino acids have been deleted.

According to the invention, the two fatty acid radicals may have the formula R—CO—, wherein R is a $C_7$–$C_{25}$-alkyl, $C_7$–$C_{25}$-alkenyl or $C_7$–$C_{25}$-alkynyl radical, unsaturated radicals preferably being present in the cis configuration. Examples of $C_7$–$C_{25}$-alkyl, -alkenyl and -alkynyl radicals are $C_{16}$ and $C_{18}$ radicals.

According to the invention there is also provided a composition comprising a S-(2,3-dihydroxypropyl)-cysteine peptide according to the invention together with a conventional carrier and/or adjuvant. The composition according to the invention can be used for stimulating the synthesis of antibodies, for preventing infections (anti-infective activity), as an immunostimulant against tumours, for activating macro-phages, for developing tolerance towards endotoxins or in the case of septic shock, especially in the case of Gram-negative bacteria, or as a vaccine adjuvant (admixture with a vaccine).

According to the invention, S-(2,3-dihydroxypropyl)-cysteine peptides can be prepared in a fully synthetic manner. The person skilled in the art can proceed analogously to the cited prior art. Reference is made also to DE 35 46 150 A1, DE 37 00 173 A1, DE 38 13 821 A1, DE 41 19 856 A1 and DE 43 29 309 A1.

The invention is explained in greater detail below with reference to an Example.

EXAMPLE

The lipopeptide is prepared from *Mycoplasma fermentans* (for example PG18). The isolation of the lipopeptide from mycoplasma is carried out by the following known separation procedure (Mühlradt et al. in Biochemistry, 35 (1996) 7781–7786).

(i) Delipidation of the mycoplasma using chloroform/methanol.

(ii) Extraction of the delipidated mycoplasma using hot 25 mM octyl glucoside.

(iii) Dialysis of the detergent extract.

(iv) Concentration of the extract by lyophilisation.

(v) Reversed-phase chromatography on a C8 column using a water/2-propanol gradient.

Detection of the biological activity is effected by measuring nitrite and nitrate as the secondary products of nitrogen monoxide, which is liberated on stimulation of interferon-treated murine peritoneal macrophages.

The active ingredient is a S-(2,3-dihydroxypropyl)-cysteine peptide which has two long-chain fatty acids (C16:0 and C18:0/C18:1) bonded in the form of esters at the dihydroxypropyl group, and which has the following (SEQ ID NO 1):

```
Dhc-GNN DES NIS FKE K  (SEQ ID NO 1).
    1   5   10
```

The most frequent molecular weight is 2164 g/mol. In addition, it is possible to find variants which are distinguished by different fatty acids and by a peptide that is shortened by two C-terminal amino acids.

The substance has the property of stimulating macrophages of mice and humans to release cytokines and prostaglandins, with all the consequences of indirect stimulation of T and B lymphocytes; see Mu hlradt et al. in Infect. Immun., 59 (1991) 3962–3968 and Feng & Lo in Infect. Immun., 62 (1994) 3916–3921. Its half-maximum effective concentration (Max/2) is 20 pg/ml or $10^{-11}$ M in the mouse system. That effective concentration is lower by a factor of from $10^2$ to $10^3$ than the corresponding known concentrations of similar natural or synthetic lipopeptides.

What is claimed is:

1. A composition for activating macrophages comprising S-(2,3-Dihydroxypropyl)-cysteine (Dhc)-peptide having two fatty acids, which fatty acids may be identical or different, bonded in the form of esters to the dihydroxypropyl group, the peptide having the following amino acid sequence (SEQ ID No 1):

DhcGN NDE SNI SFK EK (SEQ ID No 1)
          2    5    10 or an amino acid sequence that is identical to sequence (SEQ ID No 1) with an exception selected from the following group:
  (i) that the N-terminal amino acids in positions 2 (G=glycine) and, optionally 3, (N=asparagine) are absent,
  (ii) that the N-terminal amino acids in position 2 (G=glycine) and, optionally 3 (N=asparagine), are absent and one or two C-terminal amino acids are absent, and
  (iii) that one or two C-terminal amino acids are absent.

2. The composition according to claim 1 wherein the two fatty acid radicals have the formula R—CO—, wherein R is selected from the group consisting of a $C_7$–$C_{25}$-alkyl, $C_7$–$C_{25}$-alkenyl and $C_7$–$C_{25}$-alkynyl group.

3. The composition according to claim 2 wherein the $C_7$–$C_{25}$-alkenyl group contains unsaturated C=C double bonds, the configuration of which is cis, trans or mixtures thereof.

4. The composition according to claim 1 further comprising at least one of a conventional excipient or additive.

5. The composition according to claim 1 further comprising a conventional excipient and an additive.

6. A method of stimulating the synthesis of antibodies, comprising the step of administering the composition according to claim 1 together with a conventional excipient or additive or excipient and additive to humans or animals.

7. A method of activating macrophages, comprising the step of administering the composition according to claim 1 together with a conventional excipient or additive or excipient and additive to humans or animals.

8. A method of stimulating the synthesis of antibodies comprising the step of administering the composition according to claim 1 together with a excipient or additive or excipient and in admixture with a known vaccine to humans or animals.

9. A method of activating macrophages, comprising the step of administering the composition according to claim 1 together with a conventional excipient or additive or excipient and additive in admixture with a vaccine.

10. An immunological preparation comprising the S-(2,3-dihydroxypropyl)-cysteine (Dhc) peptide according to claim 1 for stimulation the synthesis of antibodies together with a excipient or additive or excipient and additive.

11. An immunological preparation comprising the S-(2,3-dihydroxypropyl)-cysteine (Dhc) peptide according to claim 1 for activation macrophages together with a excipient or additive or excipient and additive.

12. An immunological adjuvant preparation comprising the S-(2,3-dihydroxypropyl)-cysteine (Dhc) peptide according to claim 1 and an additive, excipient or additive and excipient for stimulating the synthesis of antibodies.

13. An immunological adjuvant preparation comprising the S-(2,3-dihydroxypropyl)-cysteine (Dhc) peptide according to claim 1 and an additive, excipient or additive and excipient for activating macrophages.

\* \* \* \* \*

UNITED STATES PATENT AND TRADEMARK OFFICE
CERTIFICATE OF CORRECTION

PATENT NO. : 6,573,242 B1
DATED : June 3, 2003
INVENTOR(S) : Peter F. Muehlradt

It is certified that error appears in the above-identified patent and that said Letters Patent is hereby corrected as shown below:

<u>Title page,</u>
Item [73], Assignee, change "Gesellschaft fuer Biotechnologische" to
-- Gesellschaft fuer Biotechnologische Forschung mbH --.

Signed and Sealed this

Twenty-first Day of October, 2003

JAMES E. ROGAN
*Director of the United States Patent and Trademark Office*

SEQUENCE LISTING

```
<160> NUMBER OF SEQ ID NOS: 2

<210> SEQ ID NO 1
<211> LENGTH: 14
<212> TYPE: PRT
<213> ORGANISM: Mycoplasma fermentans
<220> FEATURE:
<221> NAME/KEY: MOD_RES
<222> LOCATION: (1)..(1)
<223> OTHER INFORMATION: X is S-(2,3-dihydroxypropyl)-cysteine

<400> SEQUENCE: 1

Xaa Gly Asn Asn Asp Glu Ser Asn Ile Ser Phe Leu Glu Leu
1               5                   10

<210> SEQ ID NO 2
<211> LENGTH: 10
<212> TYPE: PRT
<213> ORGANISM: Rhodopseudomonas Viridis
<220> FEATURE:
<221> NAME/KEY: MOD_RES
<222> LOCATION: (1)..(1)
<223> OTHER INFORMATION: X is S-(2,3-dihydroxypropyl)-cysteine

<400> SEQUENCE: 2

Xaa Phe Glu Pro Pro Pro Ala Thr Thr Thr
1               5                   10
```